US00PP27257P2

(12) United States Plant Patent
van den Hoogen

(10) Patent No.: US PP27,257 P2
(45) Date of Patent: Oct. 11, 2016

(54) ***VERONICA* PLANT NAMED 'ALLCHOICE'**

(50) Latin Name: *Veronica longifolia*
Varietal Denomination: Allchoice

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 176 days.

(21) Appl. No.: 14/121,540

(22) Filed: Sep. 17, 2014

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Keith Robinson
(74) *Attorney, Agent, or Firm* — C. A. Whealy

(57) ABSTRACT

A new and distinct cultivar of *Veronica* plant named 'Allchoice', characterized by its upright plant habit; freely flowering habit; compact and dense inflorescences with numerous soft pink-colored flowers; long flowering period; and used as a garden or container plant.

3 Drawing Sheets

Botanical designation: *Veronica longifolia.*
Cultivar denomination: 'ALLCHOICE'.

BACKGROUND OF THE INVENTION

The present invention relates to a new and distinct cultivar of *Veronica* plant, botanically known as *Veronica longifolia* and hereinafter referred to by the name 'Allchoice'.

The new *Veronica* plant is a product of a planned breeding program conducted by the Inventor in Cuijk, The Netherlands. The objective of the breeding program is to create new attractive *Veronica* plants that can be used as a garden or container plant.

The new *Veronica* plant originated from an open-pollination in June, 2002 of a proprietary selection of *Veronica longifolia* identified as code number BP-98, not patented, as the female, or seed, parent with an unknown selection of *Veronica longifolia* as the male, or pollen, parent. The new *Veronica* plant was discovered and selected by the Inventor as a single flowering plant from within the progeny of the stated open-pollination in a controlled environment in Cuijk, The Netherlands in June, 2004.

Asexual reproduction of the new *Veronica* plant by vegetative cuttings in a controlled environment in Cuijk, The Netherlands, since July, 2004 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allchoice'. These characteristics in combination distinguish 'Allchoice' as a new and distinct *Veronica* plant:

1. Upright plant habit.
2. Freely flowering habit.
3. Compact and dense inflorescences with numerous soft pink-colored flowers.
4. Long flowering period.
5. Can be used as a garden or container plant.

Plants of the new *Veronica* differ primarily from plants of the female parent selection in plant habit as plants of the new *Veronica* are more uniform than plants of the female parent selection.

Plants of the new *Veronica* can be compared to plants of *Veronica longifolia* 'Alllove', disclosed in U.S. Plant Pat. No. 21,478. In side-by-side comparisons conducted in Cuijk, The Netherlands, plants of the new *Veronica* differed primarily from plants of 'Alllove' in the following characteristics:

1. Plants of the new *Veronica* had fewer lateral branches than plants of 'Alllove'.
2. Inflorescences of plants of the new *Veronica* were less dense than inflorescences of 'Alllove'.
3. Plants of the new *Veronica* and 'Alllove' differed in flower color as plants of 'Alllove' had red purple-colored flowers.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Allchoice'.

The photograph on the second sheet is a close-up view of typical inflorescences of 'Allchoice'.

The photograph on the third sheet is a close-up view of the upper surface of a typical leaf of 'Allchoice'.

DETAILED BOTANICAL DESCRIPTION

Plants used for the aforementioned photographs and following description were grown during the spring and early summer in ground beds in an outdoor nursery in Rijswijk, The Netherlands and under cultural practices typical of commercial production. During the production of the plants, day temperatures ranged from 15° C. to 30° C. and night temperatures ranged from 4° C. to averaged 17° C. Plants were five months old when the photographs and the description were taken. In the following description, color references are made to The Royal Horticultural Society Colour Chart, 2007 Edition, except where general terms of ordinary dictionary significance are used.

Botanical classification: *Veronica longifolia* 'Allchoice'.

Parentage:

*Female, or seed, parent*.—Proprietary selection of *Veronica longifolia* identified as code number BP-98, not patented.

*Male, or pollen, parent*.—Unknown selection of *Veronica longifolia*, not patented.

Propagation:

*Type cutting*.—Vegetative cuttings.

*Time to initiate roots, summer*.—About 10 to 14 days at temperatures about 12° C. to 30° C.

*Time to produce a rooted young plant, summer*.—About 24 to 32 days at temperatures about 12° C. to 30° C.

*Root description*.—Fine, fleshy.

*Rooting habit*.—Freely branching; dense.

Plant description:

*Plant type*.—Herbaceous perennial.

*Plant and growth habit*.—Broadly upright inverted triangle; freely basal branching habit with about 18 main stems; moderately vigorous growth habit.

*Plant height*.—About 40.5 cm.

*Plant width*.—About 29.2 cm.

*Lateral branch description*.—Length: About 20.7 cm. Diameter: About 2.5 mm. Internode length: About 3.3 cm. Strength: Strong. Texture: Densely pubescent. Color: Close to 143B.

Leaf description:

*Arrangement*.—Opposite, simple.

*Length*.—About 5.6 cm.

*Width*.—About 2.8 cm.

*Shape*.—Ovate to lanceolate; slightly carinate.

*Apex*.—Acute.

*Base*.—Truncate.

*Margin*.—Serrate.

*Texture, upper surface*.—Moderately pubescent.

*Texture, lower surface*.—Pubescent along the main vein.

*Venation pattern*.—Pinnate.

*Color*.—Developing leaves, upper surface: Close to 143A. Developing leaves, lower surface: Close to 143C. Fully expanded leaves, upper surface: Close to N137A; venation, close to 143A. Fully expanded leaves, lower surface: Between 137C and 147B; venation, close to 143B.

*Petiole length*.—About 1.2 cm.

*Petiole diameter*.—About 2 mm by 1.5 mm.

*Petiole texture, upper and lower surfaces*.—Smooth.

*Petiole color, upper and lower surfaces*.—Close to 143C.

Flower description:

*Flower arrangement and shape*.—Single campanulate flowers arranged on primary and secondary terminal racemes; racemes compact and dense; flowers face mostly outwardly.

*Flowering habit*.—Freely flowering, each terminal branch has one primary raceme and several secondary racemes; about 250 flowers develop per primary inflorescence.

*Fragrance*.—None detected.

*Natural flowering season*.—Plants begin flowering about eight weeks after pinching; long flowering period, flowering continuous from July to late September in The Netherlands.

*Flower longevity on the plant*.—About one week; flowers not persistent.

*Flower buds*.—Length: About 5 mm. Diameter: About 2.5 mm. Shape: Oblong. Color: Close to 68D.

*Inflorescence height*.—About 11 cm.

*Inflorescence diameter*.—About 2 cm.

*Flower diameter*.—About 8 mm.

*Flower height*.—About 9 mm.

*Petals*.—Quantity and arrangement: About four in a single whorl, petals fused about 40% of the length from the base. Length: About 5 mm. Width: About 3 mm to 4 mm. Shape: Oblanceolate. Apex: Obtuse. Margin: Entire. Texture, upper and lower surfaces: Smooth, glabrous. Color: When opening, upper and lower surfaces: Close to between 73C and 73D. Fully opened, upper and lower surfaces: Close to between 65B and 65C; color becoming closer to 65C with development.

*Sepals*.—Quantity and arrangement: About four in a single whorl, sepals fused about 5% of the length from the base. Length: About 2.5 mm to 3 mm. Width: About 0.75 mm. Shape: Narrowly ovate. Apex: Acute. Margin: Entire. Texture, upper and lower surfaces: Smooth, glabrous. Color: When opening, upper and lower surfaces: Close to 137A. Fully opened, upper and lower surfaces: Close to 137A.

*Peduncles*.—Length: About 10.7 cm. Diameter: About 2 mm. Aspect: Mostly upright. Strength: Strong. Texture: Smooth, glabrous. Color: Close to 143C.

*Pedicels*.—Length: About 1 mm. Diameter: About 0.5 mm. Aspect: About 45° from peduncle axis. Strength: Strong. Texture: Smooth, glabrous. Color: Close to 138A.

*Reproductive organs*.—Stamens: Quantity per flower: Two. Filament length: About 5 mm. Filament color: Close to 65C. Anther length: About 1 mm. Anther shape: Elliptical. Anther color: Close to 75D. Pollen amount: Moderate. Pollen color: Close to 4D. Pistils: Quantity per flower: One. Pistil length: About 8 mm. Stigma shape: Clavate. Stigma color: Close to 83C. Style length: About 7.5 mm. Style color: Close to 75B. Ovary color: Close to 143A.

*Seeds and fruits*.—Seed and fruit development has not been observed on plants of the new *Veronica*.

Disease & pest resistance: Plants of the new *Veronica* have not been noted to be resistant to pathogens and pests common to *Veronica* plants.

Garden performance: Plants of the new *Veronica* have exhibited good garden performance and to be tolerant to rain, wind, high temperatures of about 35° C. and to be hardy to USDA Hardiness Zone 4.

It is claimed:

1. A new and distinct *Veronica* plant named 'Allchoice' as illustrated and described.

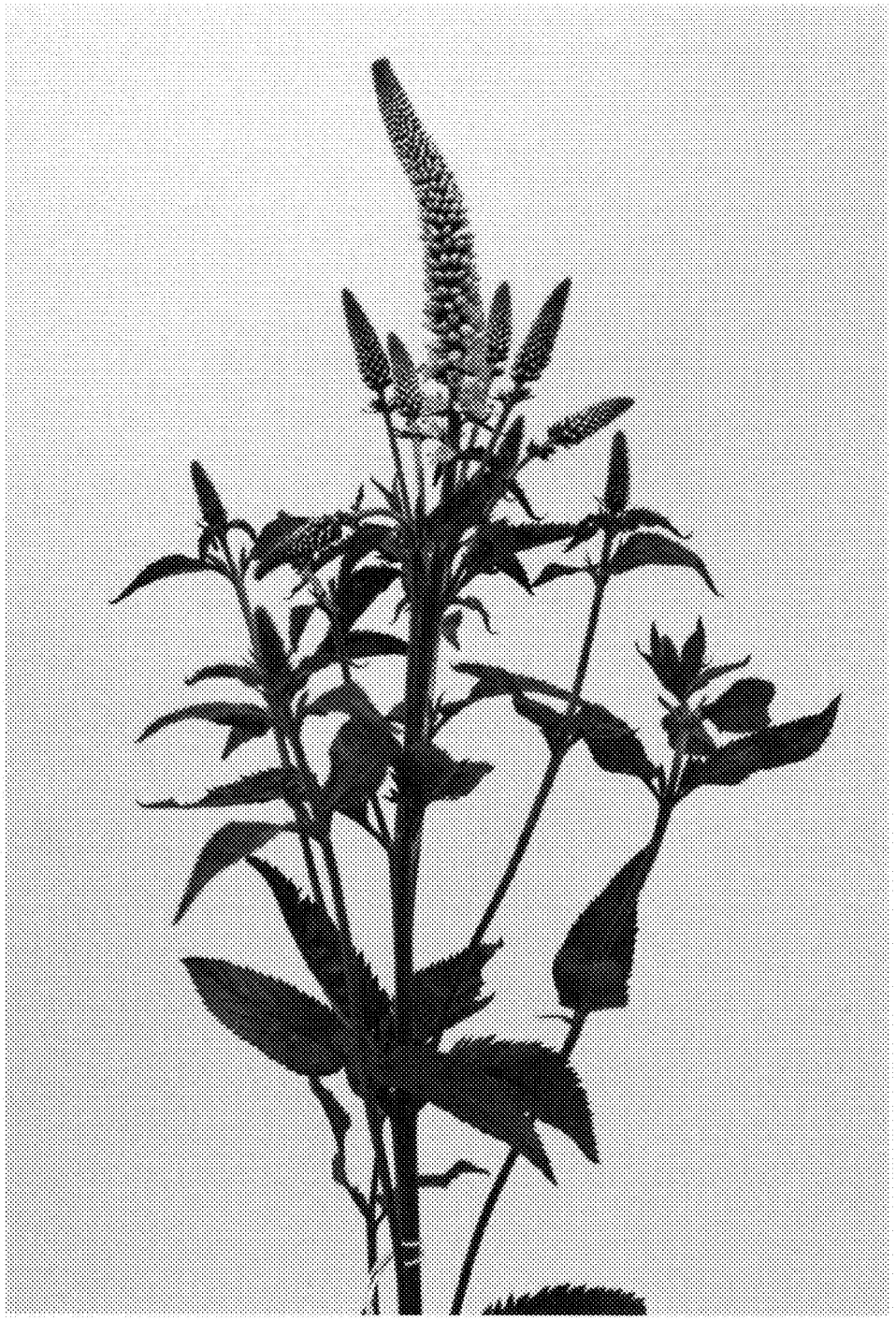

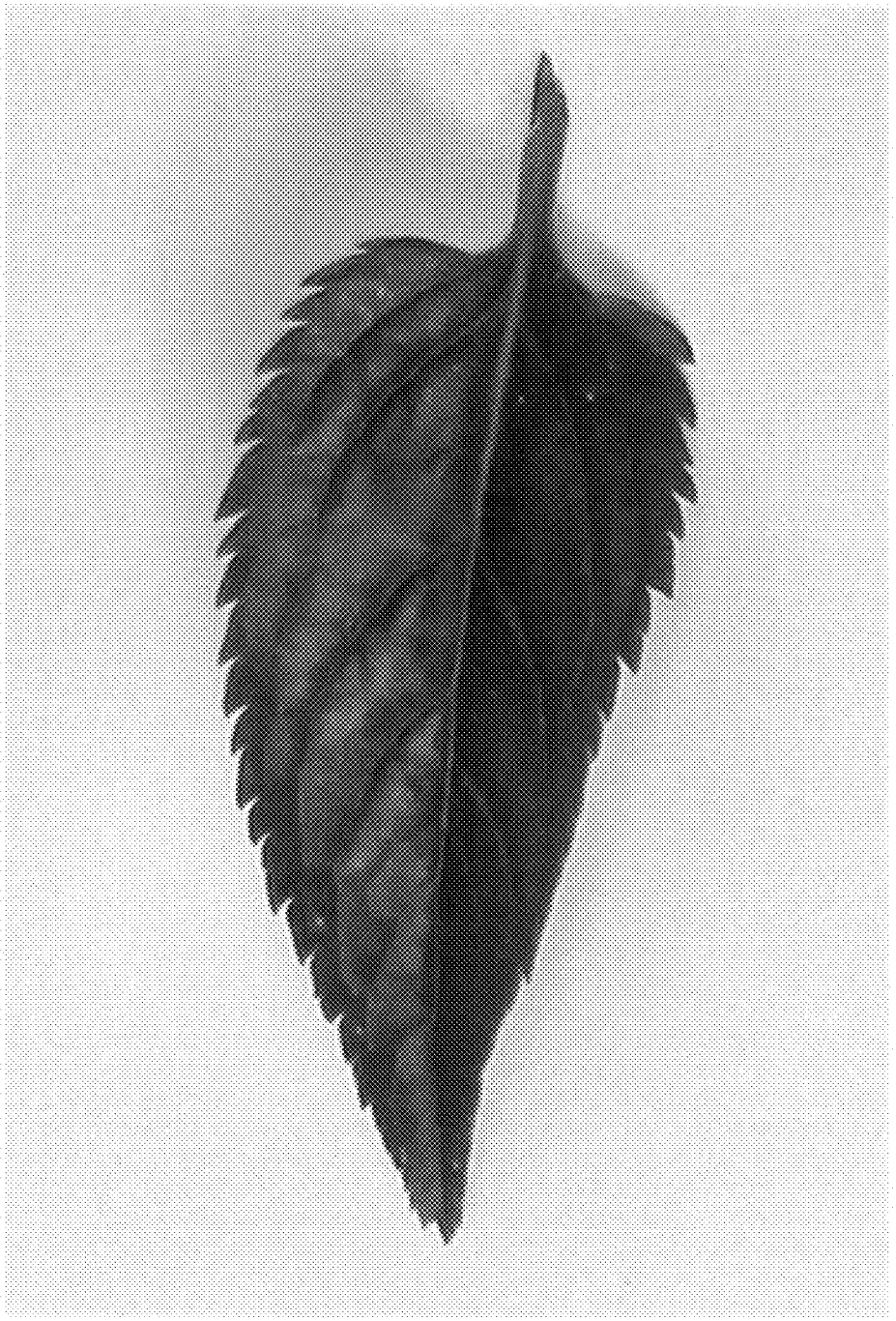

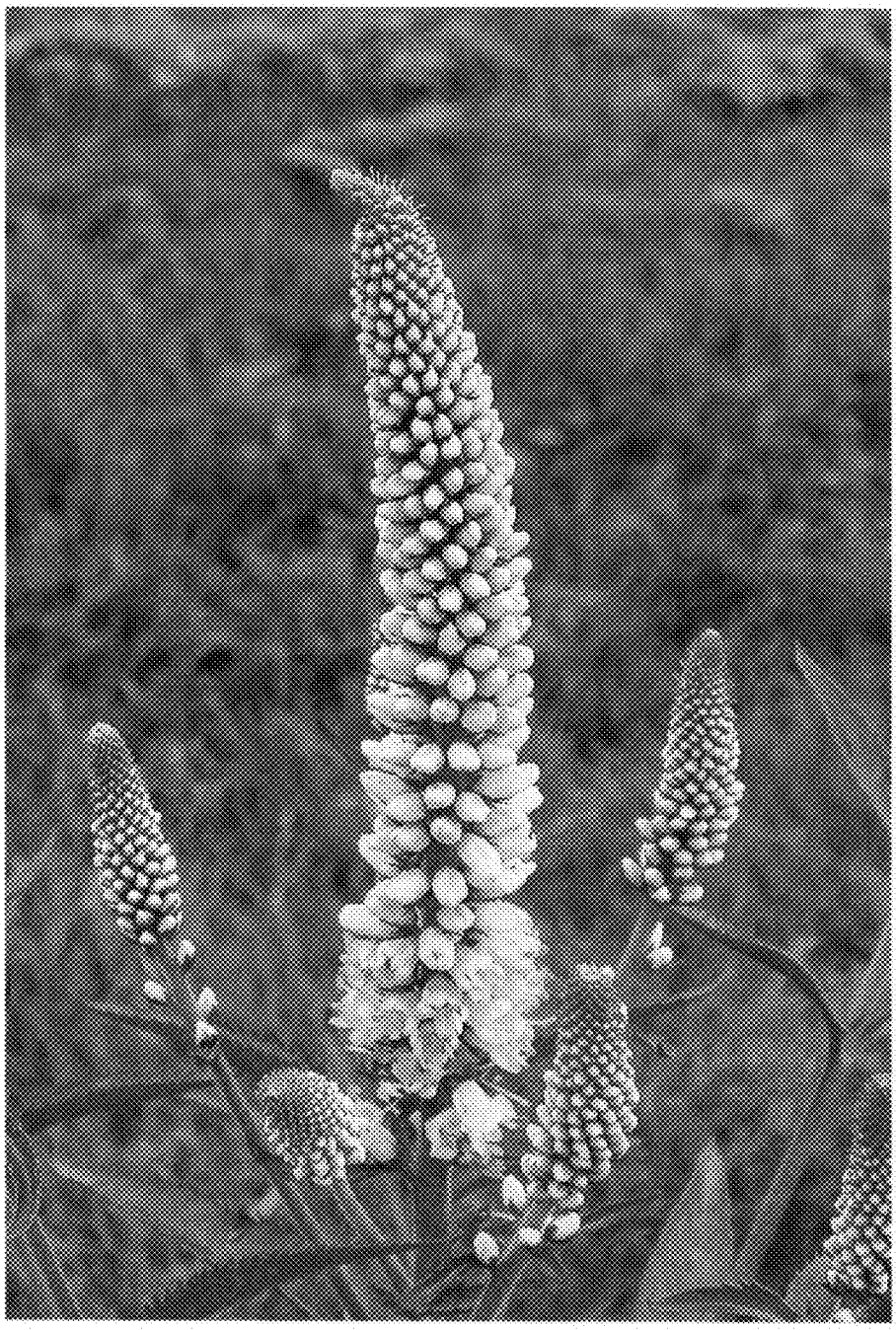

* * * * *